(12) United States Patent
Boutelle

(10) Patent No.: US 8,515,511 B2
(45) Date of Patent: Aug. 20, 2013

(54) SENSOR WITH AN OPTICAL COUPLING MATERIAL TO IMPROVE PLETHYSMOGRAPHIC MEASUREMENTS AND METHOD OF USING THE SAME

(75) Inventor: Steve Boutelle, Longmont, CO (US)

(73) Assignee: Covidien LP, Mansfield, MA (US)

( * ) Notice: Subject to any disclaimer, the term of this patent is extended or adjusted under 35 U.S.C. 154(b) by 957 days.

(21) Appl. No.: 12/568,952

(22) Filed: Sep. 29, 2009

(65) Prior Publication Data

US 2011/0077483 A1    Mar. 31, 2011

(51) Int. Cl.
*A61B 5/1455* (2006.01)
(52) U.S. Cl.
USPC ............ 600/323; 600/310; 600/322; 600/344
(58) Field of Classification Search
USPC ................. 600/310, 316, 322, 323, 326, 336, 600/338, 340, 344, 473, 476; 257/433
See application file for complete search history.

(56) References Cited

U.S. PATENT DOCUMENTS

| | | | |
|---|---|---|---|
| 3,638,640 A | 2/1972 | Shaw | |
| 4,321,930 A | 3/1982 | Jobsis et al. | |
| 4,380,240 A | 4/1983 | Jobsis et al. | |
| 4,510,938 A | 4/1985 | Jobsis et al. | |
| 4,685,464 A | 8/1987 | Goldberger et al. | |
| 4,714,341 A | 12/1987 | Hamaguri et al. | |
| 4,805,623 A | 2/1989 | Jöbsis | |
| 4,807,631 A | 2/1989 | Hersh et al. | |
| 4,865,038 A * | 9/1989 | Rich et al. ..................... | 600/344 |
| 4,880,304 A | 11/1989 | Jaeb et al. | |
| 4,911,167 A | 3/1990 | Corenman et al. | |
| 4,913,150 A | 4/1990 | Cheung et al. | |
| 4,936,679 A | 6/1990 | Mersch | |
| 4,938,218 A | 7/1990 | Goodman et al. | |
| 4,971,062 A | 11/1990 | Hasebe et al. | |
| 4,972,331 A | 11/1990 | Chance | |
| 4,974,591 A | 12/1990 | Awazu et al. | |
| 5,028,787 A | 7/1991 | Rosenthal et al. | |
| 5,040,539 A | 8/1991 | Schmitt et al. | |
| 5,054,488 A | 10/1991 | Muz | |
| 5,055,671 A | 10/1991 | Jones | |
| 5,065,749 A | 11/1991 | Hasebe et al. | |
| 5,084,327 A | 1/1992 | Stengel | |
| 5,104,623 A | 4/1992 | Miller | |

(Continued)

FOREIGN PATENT DOCUMENTS

| | | |
|---|---|---|
| DE | 19632361 | 2/1997 |
| EP | 0127947 | 12/1984 |

(Continued)

OTHER PUBLICATIONS

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

According to various embodiments, a medical sensor assembly may include an optical coupling material configured to prevent undesired light from being detected and to enhance the amount of light received at the detector. The optical coupling material may be a gel, liquid, oil, or other non-solid material with appropriate optical properties.

20 Claims, 5 Drawing Sheets

(56) References Cited

U.S. PATENT DOCUMENTS

| | | | |
|---|---|---|---|
| 5,109,849 A * | 5/1992 | Goodman et al. | 600/483 |
| 5,119,815 A | 6/1992 | Chance | |
| 5,122,974 A | 6/1992 | Chance | |
| 5,145,565 A * | 9/1992 | Kater et al. | 600/341 |
| 5,167,230 A | 12/1992 | Chance | |
| 5,190,038 A | 3/1993 | Polson et al. | |
| 5,246,003 A | 9/1993 | DeLonzor | |
| 5,247,931 A | 9/1993 | Norwood | |
| 5,247,932 A | 9/1993 | Chung et al. | |
| 5,263,244 A | 11/1993 | Centa et al. | |
| 5,275,159 A | 1/1994 | Griebel | |
| 5,279,295 A | 1/1994 | Martens et al. | |
| 5,297,548 A | 3/1994 | Pologe | |
| 5,337,744 A | 8/1994 | Branigan | |
| 5,355,880 A | 10/1994 | Thomas et al. | |
| 5,372,136 A | 12/1994 | Steuer et al. | |
| 5,385,143 A | 1/1995 | Aoyagi | |
| 5,390,670 A | 2/1995 | Centa et al. | |
| 5,413,099 A | 5/1995 | Schmidt et al. | |
| 5,452,717 A | 9/1995 | Branigan et al. | |
| 5,469,845 A | 11/1995 | DeLonzor et al. | |
| 5,482,036 A | 1/1996 | Diab et al. | |
| 5,483,646 A | 1/1996 | Uchikoga | |
| 5,553,614 A | 9/1996 | Chance | |
| 5,564,417 A | 10/1996 | Chance | |
| 5,575,285 A | 11/1996 | Takanashi et al. | |
| 5,611,337 A | 3/1997 | Bukta | |
| 5,630,413 A | 5/1997 | Thomas et al. | |
| 5,638,818 A | 6/1997 | Diab et al. | |
| 5,645,059 A | 7/1997 | Fein et al. | |
| 5,645,060 A | 7/1997 | Yorkey | |
| 5,661,302 A | 8/1997 | Evans et al. | |
| 5,666,952 A | 9/1997 | Fuse et al. | |
| 5,680,857 A | 10/1997 | Pelikan et al. | |
| 5,692,503 A | 12/1997 | Keunstner | |
| 5,730,124 A | 3/1998 | Yamauchi | |
| D393,830 S | 4/1998 | Tobler et al. | |
| 5,758,644 A | 6/1998 | Diab et al. | |
| 5,779,631 A | 7/1998 | Chance | |
| 5,782,757 A | 7/1998 | Diab et al. | |
| 5,786,592 A | 7/1998 | Hök | |
| 5,790,729 A | 8/1998 | Pologe et al. | |
| 5,823,951 A * | 10/1998 | Messerschmidt | 600/322 |
| 5,830,136 A | 11/1998 | DeLonzor et al. | |
| 5,830,139 A | 11/1998 | Abreu | |
| 5,831,598 A | 11/1998 | Kauffert et al. | |
| 5,842,981 A | 12/1998 | Larsen et al. | |
| 5,871,442 A | 2/1999 | Madarasz et al. | |
| 5,873,821 A | 2/1999 | Chance et al. | |
| 5,920,263 A | 7/1999 | Huttenhoff et al. | |
| 5,995,855 A | 11/1999 | Kiani et al. | |
| 5,995,856 A | 11/1999 | Mannheimer et al. | |
| 5,995,859 A | 11/1999 | Takahashi | |
| 6,011,986 A | 1/2000 | Diab et al. | |
| 6,064,898 A | 5/2000 | Aldrich | |
| 6,081,742 A | 6/2000 | Amano et al. | |
| 6,088,607 A | 7/2000 | Diab et al. | |
| 6,120,460 A | 9/2000 | Abreu | |
| 6,134,460 A | 10/2000 | Chance | |
| 6,144,444 A | 11/2000 | Haworth et al. | |
| 6,150,951 A | 11/2000 | Olejniczak | |
| 6,154,667 A | 11/2000 | Miura et al. | |
| 6,163,715 A | 12/2000 | Larsen et al. | |
| 6,181,958 B1 | 1/2001 | Steuer et al. | |
| 6,181,959 B1 | 1/2001 | Schöllermann et al. | |
| 6,192,260 B1 | 2/2001 | Chance | |
| 6,230,035 B1 | 5/2001 | Aoyagi et al. | |
| 6,256,523 B1 | 7/2001 | Diab et al. | |
| 6,261,236 B1 | 7/2001 | Grimblatov | |
| 6,266,546 B1 | 7/2001 | Steuer et al. | |
| 6,285,895 B1 | 9/2001 | Ristolainen et al. | |
| 6,312,393 B1 | 11/2001 | Abreu | |
| 6,353,750 B1 | 3/2002 | Kimura et al. | |
| 6,397,091 B2 | 5/2002 | Diab et al. | |
| 6,415,236 B2 | 7/2002 | Kobayashi et al. | |
| 6,419,671 B1 | 7/2002 | Lemberg | |
| 6,438,399 B1 | 8/2002 | Kurth | |
| 6,461,305 B1 | 10/2002 | Schnall | |
| 6,466,809 B1 | 10/2002 | Riley | |
| 6,487,439 B1 | 11/2002 | Skladnev et al. | |
| 6,501,974 B2 | 12/2002 | Huiku | |
| 6,501,975 B2 | 12/2002 | Diab et al. | |
| 6,512,937 B2 | 1/2003 | Blank et al. | |
| 6,525,386 B1 | 2/2003 | Mills et al. | |
| 6,526,301 B2 | 2/2003 | Larsen et al. | |
| 6,544,193 B2 | 4/2003 | Abreu | |
| 6,546,267 B1 | 4/2003 | Sugiura et al. | |
| 6,549,795 B1 | 4/2003 | Chance | |
| 6,564,088 B1 | 5/2003 | Soller et al. | |
| 6,580,086 B1 | 6/2003 | Schulz et al. | |
| 6,587,703 B2 | 7/2003 | Cheng et al. | |
| 6,589,172 B2 | 7/2003 | Williams et al. | |
| 6,591,122 B2 | 7/2003 | Schmitt | |
| 6,594,513 B1 | 7/2003 | Jobsis et al. | |
| 6,597,931 B1 | 7/2003 | Cheng et al. | |
| 6,606,509 B2 | 8/2003 | Schmitt | |
| 6,606,511 B1 | 8/2003 | Ali et al. | |
| 6,615,064 B1 | 9/2003 | Aldrich | |
| 6,618,042 B1 | 9/2003 | Powell | |
| 6,618,614 B1 | 9/2003 | Chance | |
| 6,622,095 B2 | 9/2003 | Kobayashi et al. | |
| 6,654,621 B2 | 11/2003 | Palatnik et al. | |
| 6,654,624 B2 | 11/2003 | Diab et al. | |
| 6,658,276 B2 | 12/2003 | Kianl et al. | |
| 6,658,277 B2 | 12/2003 | Wasserman | |
| 6,662,030 B2 | 12/2003 | Khalil et al. | |
| 6,668,183 B2 | 12/2003 | Hicks et al. | |
| 6,671,526 B1 | 12/2003 | Aoyagi et al. | |
| 6,671,528 B2 | 12/2003 | Steuer et al. | |
| 6,678,543 B2 | 1/2004 | Diab et al. | |
| 6,684,090 B2 | 1/2004 | Ali et al. | |
| 6,690,958 B1 | 2/2004 | Walker et al. | |
| 6,697,658 B2 | 2/2004 | Al-Ali | |
| 6,708,048 B1 | 3/2004 | Chance | |
| 6,711,424 B1 | 3/2004 | Fine et al. | |
| 6,711,425 B1 | 3/2004 | Reuss | |
| 6,711,426 B2 | 3/2004 | Benaron et al. | |
| 6,714,245 B1 | 3/2004 | Ono | |
| 6,719,686 B2 | 4/2004 | Coakley et al. | |
| 6,731,274 B2 | 5/2004 | Powell | |
| 6,785,568 B2 | 8/2004 | Chance | |
| 6,791,689 B1 | 9/2004 | Weckstrom | |
| 6,792,300 B1 | 9/2004 | Diab et al. | |
| 6,793,654 B2 | 9/2004 | Lemberg | |
| 6,801,797 B2 | 10/2004 | Mannheimer et al. | |
| 6,801,798 B2 | 10/2004 | Geddes et al. | |
| 6,801,799 B2 | 10/2004 | Mendelson | |
| 6,813,511 B2 | 11/2004 | Diab et al. | |
| 6,829,496 B2 | 12/2004 | Nagai et al. | |
| 6,850,053 B2 | 2/2005 | Daalmans et al. | |
| 6,863,652 B2 | 3/2005 | Huang et al. | |
| 6,873,865 B2 | 3/2005 | Steuer et al. | |
| 6,889,153 B2 | 5/2005 | Dietiker | |
| 6,898,451 B2 | 5/2005 | Wuori | |
| 6,916,289 B2 | 7/2005 | Schnall | |
| 6,939,307 B1 | 9/2005 | Dunlop | |
| 6,947,780 B2 | 9/2005 | Scharf | |
| 6,949,081 B1 | 9/2005 | Chance | |
| 6,954,663 B2 | 10/2005 | Hall | |
| 6,961,598 B2 | 11/2005 | Diab | |
| 6,971,580 B2 | 12/2005 | Zhu et al. | |
| 6,983,178 B2 | 1/2006 | Fine et al. | |
| 6,992,751 B2 | 1/2006 | Okita et al. | |
| 6,993,371 B2 | 1/2006 | Kiani et al. | |
| 6,996,427 B2 | 2/2006 | Ali et al. | |
| 7,024,235 B2 | 4/2006 | Melker et al. | |
| 7,027,849 B2 | 4/2006 | Al-Ali | |
| 7,030,749 B2 | 4/2006 | Al-Ali | |
| 7,035,697 B1 | 4/2006 | Brown | |
| 7,047,054 B2 | 5/2006 | Benni | |
| 7,047,056 B2 | 5/2006 | Hannula et al. | |
| 7,062,306 B2 | 6/2006 | Benaron et al. | |
| 7,107,116 B2 | 9/2006 | Geng et al. | |
| 7,127,278 B2 | 10/2006 | Melker et al. | |

| | | |
|---|---|---|
| 7,162,306 B2 | 1/2007 | Caby et al. |
| 7,198,778 B2 | 4/2007 | Achilefu et al. |
| 7,209,775 B2 | 4/2007 | Bae et al. |
| 7,236,811 B2 | 6/2007 | Schmitt |
| 7,242,997 B2 | 7/2007 | Geng et al. |
| 7,263,395 B2 | 8/2007 | Chan et al. |
| 7,272,426 B2 | 9/2007 | Schmid |
| 7,289,837 B2 | 10/2007 | Mannheimer et al. |
| 7,313,427 B2 | 12/2007 | Benni |
| 7,373,193 B2 | 5/2008 | Al-Ali et al. |
| 7,427,165 B2 | 9/2008 | Benaron et al. |
| 7,469,158 B2 | 12/2008 | Cutler et al. |
| 7,572,229 B2 | 8/2009 | Yeo et al. |
| 7,574,244 B2 | 8/2009 | Eghbal et al. |
| 2001/0005773 A1 | 6/2001 | Larsen et al. |
| 2001/0020122 A1 | 9/2001 | Steuer et al. |
| 2001/0039376 A1 | 11/2001 | Steuer et al. |
| 2001/0044700 A1 | 11/2001 | Kobayashi et al. |
| 2002/0026106 A1 | 2/2002 | Khalil et al. |
| 2002/0035318 A1 | 3/2002 | Mannheimer et al. |
| 2002/0038079 A1 | 3/2002 | Steuer et al. |
| 2002/0042558 A1 | 4/2002 | Mendelson |
| 2002/0049389 A1 | 4/2002 | Abreu |
| 2002/0062071 A1 | 5/2002 | Diab et al. |
| 2002/0111748 A1 | 8/2002 | Kobayashi et al. |
| 2002/0133068 A1 | 9/2002 | Huiku |
| 2002/0156354 A1 | 10/2002 | Larson |
| 2002/0161287 A1 | 10/2002 | Schmitt |
| 2002/0161290 A1 | 10/2002 | Chance |
| 2002/0165439 A1 | 11/2002 | Schmitt |
| 2002/0198443 A1 | 12/2002 | Ting |
| 2003/0023140 A1 | 1/2003 | Chance |
| 2003/0055324 A1 | 3/2003 | Wasserman |
| 2003/0060693 A1 | 3/2003 | Monfre et al. |
| 2003/0139687 A1 | 7/2003 | Abreu |
| 2003/0144584 A1 | 7/2003 | Mendelson |
| 2003/0220548 A1 | 11/2003 | Schmitt |
| 2003/0220576 A1 | 11/2003 | Diab |
| 2004/0010188 A1 | 1/2004 | Wasserman |
| 2004/0054270 A1 | 3/2004 | Pewzner et al. |
| 2004/0087846 A1 | 5/2004 | Wasserman |
| 2004/0098009 A1 | 5/2004 | Boecker et al. |
| 2004/0107065 A1 | 6/2004 | Al-Ali |
| 2004/0127779 A1 | 7/2004 | Steuer et al. |
| 2004/0171920 A1 | 9/2004 | Mannheimer et al. |
| 2004/0176670 A1 | 9/2004 | Takamura et al. |
| 2004/0176671 A1 | 9/2004 | Fine et al. |
| 2004/0230106 A1 | 11/2004 | Schmitt et al. |
| 2005/0043600 A1 | 2/2005 | Diab et al. |
| 2005/0070776 A1 | 3/2005 | Mannheimer et al. |
| 2005/0075550 A1 | 4/2005 | Lindekugel |
| 2005/0080323 A1 | 4/2005 | Kato |
| 2005/0101850 A1 | 5/2005 | Parker |
| 2005/0113651 A1 | 5/2005 | Wood et al. |
| 2005/0113656 A1 | 5/2005 | Chance |
| 2005/0168722 A1 | 8/2005 | Forstner et al. |
| 2005/0177034 A1 | 8/2005 | Beaumont |
| 2005/0192488 A1 | 9/2005 | Bryenton et al. |
| 2005/0197548 A1 | 9/2005 | Dietiker |
| 2005/0203357 A1 | 9/2005 | Debreczeny et al. |
| 2005/0209516 A1 | 9/2005 | Fraden |
| 2005/0228248 A1 | 10/2005 | Dietiker |
| 2005/0267346 A1 | 12/2005 | Faber et al. |
| 2005/0283059 A1 | 12/2005 | Iyer et al. |
| 2006/0009688 A1 | 1/2006 | Lamego et al. |
| 2006/0015021 A1 | 1/2006 | Cheng |
| 2006/0020181 A1 | 1/2006 | Schmitt |
| 2006/0030763 A1 | 2/2006 | Mannheimer et al. |
| 2006/0052680 A1 | 3/2006 | Diab |
| 2006/0058683 A1 | 3/2006 | Chance |
| 2006/0064024 A1 | 3/2006 | Schnall |
| 2006/0195028 A1 | 8/2006 | Hannula et al. |
| 2006/0224058 A1 | 10/2006 | Mannheimer |
| 2006/0247501 A1 | 11/2006 | Ali |
| 2006/0258921 A1 | 11/2006 | Addison et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0264726 A1 | 11/2006 | Mannheimer et al. |
| 2006/0264727 A1 | 11/2006 | Mannheimer et al. |
| 2006/0281984 A1 | 12/2006 | Mannheimer et al. |
| 2008/0081966 A1 | 4/2008 | Debreczeny |
| 2008/0081972 A1 | 4/2008 | Debreczeny |
| 2008/0177163 A1 | 7/2008 | Wang et al. |
| 2008/0188727 A1 | 8/2008 | Benaron et al. |
| 2008/0316488 A1 | 12/2008 | Mao et al. |
| 2009/0156912 A1* | 6/2009 | Kuhn et al. ............ 600/310 |

FOREIGN PATENT DOCUMENTS

| | | |
|---|---|---|
| EP | 0615723 | 9/1994 |
| EP | 0630203 | 12/1994 |
| EP | 760476 | 3/1997 |
| EP | 805647 | 8/2000 |
| EP | 1332713 | 8/2003 |
| EP | 1469773 | 10/2004 |
| EP | 1491135 | 12/2004 |
| FR | 2685865 | 7/1993 |
| JP | 63275325 | 11/1988 |
| JP | 3170866 | 7/1991 |
| JP | 3238813 | 10/1991 |
| JP | 4332536 | 11/1992 |
| JP | 7124138 | 5/1995 |
| JP | 7136150 | 5/1995 |
| JP | 2003194714 | 7/2003 |
| JP | 2003210438 | 7/2003 |
| JP | 2004008572 | 1/2004 |
| JP | 2004113353 | 4/2004 |
| JP | 2004166775 | 6/2004 |
| JP | 2004194908 | 7/2004 |
| JP | 2004248819 | 9/2004 |
| JP | 2004290545 | 10/2004 |
| JP | 2005034472 | 2/2005 |
| WO | WO9101678 | 2/1991 |
| WO | WO9309711 | 5/1993 |
| WO | 9502358 | 1/1995 |
| WO | WO9639927 | 12/1996 |
| WO | WO9843071 | 10/1998 |
| WO | WO9932030 | 7/1999 |
| WO | WO0021438 | 4/2000 |
| WO | WO0140776 | 6/2001 |
| WO | WO0176461 | 10/2001 |
| WO | WO0176471 | 10/2001 |
| WO | 02062213 | 8/2002 |
| WO | WO03039326 | 5/2003 |
| WO | WO03063697 | 8/2003 |
| WO | WO2005099568 | 10/2005 |
| WO | WO2006110488 | 10/2006 |

OTHER PUBLICATIONS

Nuland, Roel, et al.; "Validation of Reflectance Pulse Oximetry: An Evaluation of a new Sensor in Piglets," *Journal of Clinical Monitoring*, vol. 13, pp. 43-49 (1997).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of* the 20th Annual International conference of the IEEE Engie in Medicine and Biology Society, vol. 20, No. 6, p. 3072-3075, 1998.
Such, Hans Olaf; "Optoelectronic Non-invasive Vascular Diagnostics Using multiple Wavelength and Imaging Approach," *Dissertation*, (1998).
Lutter, N., et al.; "Comparison of Different Evaluation Methods for a Multi-wavelength Pulse Oximeter," *Biomedizinische Technik*, vol. 43, (1998).
Todd, Bryan, et al.; "The Identification of Peaks in Physiological Signals," *Computers and Biomedical Research*, vol. 32, pp. 322-335 (1999).
Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).
Goldman, Julian M.; "Masimo Signal Extraction Pulse Oximetry," *Journal of Clinical Monitoring and Computing*, vol. 16, pp. 475-483 (2000).
Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.
Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).
Kaestle, S.; "Determining Artefact Sensitivity of New Pulse Oximeters in Laboratory Using Signals Obtained from Patient," *Biomedizinische Technik*, vol. 45 (2000).
Cysewska-Sobusaik, Anna; "Metrological Problems With noninvasive Transillumination of Living Tissues," *Proceedings of SPIE*, vol. 4515, pp. 15-24 (2001).
Belal, Suliman Yousef, et al.; "A fuzzy system for detecting distorted plethysmogram pulses in neonates and paediatric patients," Physiol. Meas., vol. 22, pp. 397-412 (2001).
Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Earthrowl-Gould, T., et al.; "Chest and abdominal surface motion measurement for continuous monitoring of respiratory function," *Proc. Instn Mech Engrs*, V215, Part H; pp. 515-520 (2001).
Chan, K.W., et al.; "17.3: Adaptive Reduction of Motion Artifact from Photoplethysmographic Recordings using a Variable Step-Size LMS Filter," *IEEE*, pp. 1343-1346 (2002).
Yoon, Gilwon, et al.; Multiple diagnosis based on Photoplethysmography: hematocrit, SpO2, pulse and respiration, *Optics in Health Care and Biomedical optics: Diagnostics and Treatment; Proceedings of the SPIE*, vol. 4916; pp. 185-188 (2002).
Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.
Lopez-Silva, Sonnia Maria Lopez, et al.; "Near-infrared transmittance pulse oximetry with laser diodes," *Journal of Biomedical Optics*, vol. 8, No. 3, pp. 525-533 (Jul. 2003).
Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.
Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.
Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.
Johansson, A.; "Neural network for photoplethysmographic respiratory rate monitoring," *Medical & Biological Engineering & Computing*, vol. 41, pp. 242-248 (2003).
Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).
Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.
Spigulis, Janis, et al.; "Optical multi-channel sensing of skin blood pulsations," *Optical Sensing, Proceedings of SPIE*, vol. 5459, pp. 46-53 (2004).
Huang, J., et al.; "Low Power Motion Tolerant Pulse Oximetry," *Abstracts*, A7, p. S103. (undated).
Hamilton, Patrick S., et al.; "Effect of Adaptive Motion-Artifact Reduction on QRS Detection," *Biomedical Instrumentation & Technology*, pp. 197-202 (undated).
Kim, J.M., et al.; "Signal Processing Using Fourier & Wavelet Transform," pp. II-310-II-311 (undated).
Odagiri, Y.; "Pulse Wave Measuring Device," *Micromechatronics*, vol. 42, No. 3, pp. 6-11 (undated) (Article in Japanese—contains English summary of article).
Neumann, R., et al.; "Fourier Artifact suppression Technology Provides Reliable $SpO_2$," *Abstracts*, A11, p. S105. (undated).
Ikeda, Kenji, et al.; "Improvement of Photo-Electric Plethysmograph Applying Newly Developed Opto-Electronic Devices," IEEE Tencon, pp. 1109-1112 (1999).
Yang, Boo-Ho, et al.; "Development of the ring sensor for healthcare automation," Robotics and Autonomous Systems, vol. 30, pp. 273-281 (2000).
Rhee, Sokwoo, et al.; "Artifact-Resistant, Power-Efficient Design of Finger-Ring Plethysmographic Sensor—Part I: Design and Analysis," Proceedings of the 22nd Annual EMBS International Conference, Chicago, Illinois; Jul. 23-28, 2000; pp. 2792-2795.
Aoyagi, T., et al.; "Pulse Oximeters: background, present and future," Neonatal Care, vol. 13, No. 7, pp. 21-27 (2000) (Article in Japanese—contains English summary of article).
Cubeddu, Rinaldo, et al.; "Portable 8-channel time-resolved optical imager for functional studies of biological tissues," Photon Migration, Optical Coherence Tomography, and Microscopy, Proceedings of SPIE, vol. 4431, pp. 260-265 (2001).
Rhee, Sokwoo, et al.; "Artifact-Resistant, Power-Efficient Design of Finger-Ring Plethysmographic Sensor," IEEE Transactions on Biomedical Engineering, vol. 48, No. 7, pp. 795-805 (Jul. 2001).
Lopez-Silva, Sonnia Maria Lopez, et al.; "NIR transmittance pulse oximetry system with laser diodes," Clinical Diagnostic Systems, Proceedings of SPIE, vol. 4255, pp. 80-87 (2001).
Liu, Ying, et al.; "Sensor design of new type reflectance pulse oximetry," Optics in Health Care and Biomedical Optics: Diagnostics and Treatment, Proceedings of SPIE, vol. 4916, pp. 98-102 (2002).
Tobata, H., et al.; "Study of Ambient Light Affecting Pulse Oximeter Probes," Ikigaku (Medical Technology), vol. 71, No. 10, pp. 475-476 (2002) (Article in Japanese—contains English summary of article).
Shaltis, Phillip, et al.; "Implementation and Validation of a Power-Efficient, High-Speed Modulation Design for Wireless Oxygen Saturation Measurement Systems," IEEE, pp. 193-194 (2002).
Aoyagi, Takuo; "Pulse oximetry: its invention, theory, and future," Journal of Anesthesia, vol. 17, pp. 259-266 (2003).
Mendelson, Y., et al.; "Measurement Site and Photodetector Size Considerations in Optimizing Power Consumption of a Wearable Reflectance Pulse Oximeter," Proceedings of the 25th Annual International conference of the IEEE EMBS, Cancun, Mexico, Sep. 17-21, 2003.
Itoh, K., et al.; "Pulse Oximeter," Toyaku Zasshi (Toyaku Journal), vol. 25, No. 8, pp. 50-54 (2003) (Article in Japanese—contains English summary of article).
Pujary, C., et al.; "Photodetector Size Considerations in the Design of a Noninvasive Reflectance Pulse Oximeter for Telemedicine Applications," IEEE, pp. 148-149 (2003).
Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.
Johnston, William S., et al.; "Effects of Motion Artifacts on helmet-Mounted Pulse Oximeter Sensors," 2 pgs. (2004).
Matsuzawa, Y., et al.; "Pulse Oximeter," Home Care Medicine, pp. 42-45 (Jul. 2004); (Article in Japanese—contains English summary of article).

* cited by examiner

SENSOR WITH AN OPTICAL COUPLING MATERIAL TO IMPROVE PLETHYSMOGRAPHIC MEASUREMENTS AND METHOD OF USING THE SAME

BACKGROUND

The present disclosure relates generally to medical devices and, more particularly, to sensors used for sensing physiological parameters of a patient.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry is commonly used to measure blood-oxygen saturation of hemoglobin in arterial blood and/or the rate of blood pulsations corresponding to each heartbeat of a patient.

Pulse oximeters typically utilize a non-invasive sensor that transmits light through a patient's tissue and that photoelectrically detects the transmission of light through such tissue. One or more of the above physiological characteristics may then be calculated based upon the amount of light absorbed and/or scattered in the tissue. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms.

Pulse oximetry sensors may be applied to a patient's tissue site and secured, for example by adhesives, clips, or light pressure, to achieve a conforming fit. However, even if a sensor is relatively securely fitted to the tissue, physical motion of the patient may change the fit of the sensor and introduce artifacts into the measured signal. For example, for the case a bandage-type sensor wrapped around the fingertip, if the finger is bent at a first joint, parts of the sensor may fold or buckle away from the tissue. Such small changes in the conformation of the sensor may cause the optical components to lose their contact with the skin, resulting in changes to the emitted and/or detected light, which in turn may lead to signal artifacts. While these artifacts may sometimes be addressed by signal processing and filtering to mitigate the effects, such signal processing may be complex.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
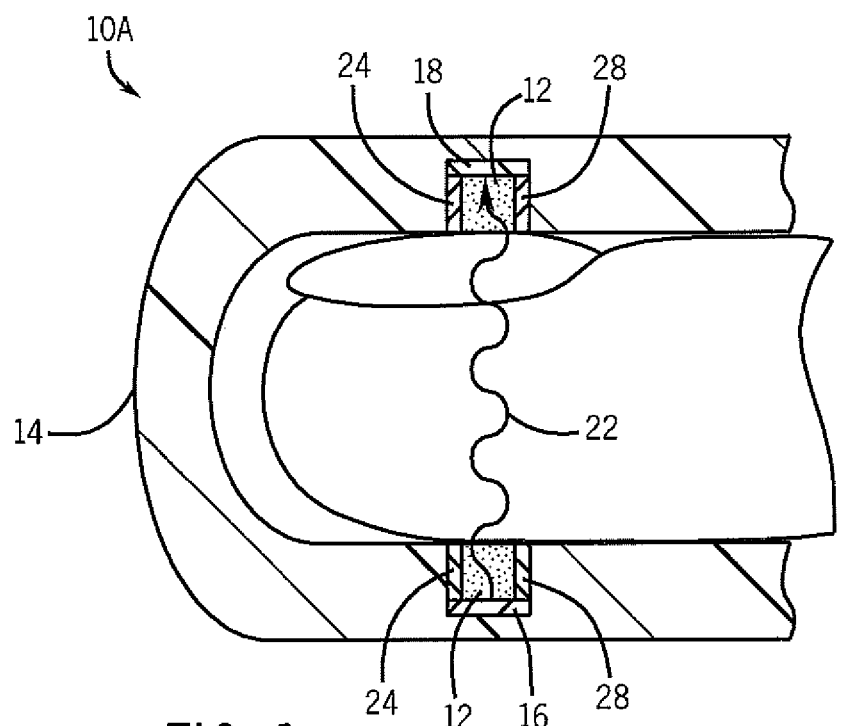
FIG. 1 is a side cross-sectional view of a transmission-type sensor including an optical coupling material applied to a digit according to certain embodiments.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Pulse oximetry sensors are typically placed on a patient in a location that is normally perfused with arterial blood to facilitate calculation of the desired blood characteristics, such as arterial oxygen saturation measurement ($SpO_2$). For example, common sensor sites include a patient's fingertips, toes, earlobes, or forehead. In addition, pulse oximetry sensors may be capable of performing intrauterine measurements. Regardless of the placement of a sensor used for pulse oximetry, the reliability of the pulse oximetry measurement is related to the accurate detection of transmitted light that has passed through the perfused tissue and that has not been supplemented by undesired light sources or that has not been scattered or redirected before passing through the tissue and being detected.

The reliability of the measurements may be influenced by signal artifacts that are the result of movement of the pulse oximetry sensor or its optical sensing components relative to the patient's tissue. For example, the sensing components (e.g., an emitter and/or a detector) may move relative to the tissue as a result of patient movement (e.g., tapping, twitching, flexing, jerking, pressing, scratching, etc.) or as a result of the patient being jostled while in care. In addition, a poor initial fit of the sensor to the tissue may contribute to signal artifacts. When the emitter and/or the detector are not in close contact with the tissue, the resultant measured signal may be degraded. Because the refractive index of air is different than refractive index of the emitter itself, emitted light that passes through an air gap between the emitter and the tissue may be refracted away from the tissue. As a result, less of the emitted light will reach the tissue and the intensity of the measured signal may be decreased. Similarly, an air gap between the tissue and the detector may result in a portion of the emitted light that has passed through the tissue being refracted away from the detector, which may further decrease the intensity of the transmitted optical signal. In addition, any gap between the tissue and the sensor may permit outside light infiltration, which may introduce inaccuracies into the measurements. In any case, a conforming fit between a patient's tissue and the emitter and detector of a sensor may improve the quality of the measured signal.

Sensors for pulse oximetry or other applications utilizing spectrophotometry may improve the quality of the measured signal by using an optical coupling material applied to one or more of the optical components of the sensor. The optical coupling material may directly couple a sensor's emitter and/or detector to the tissue, reducing any air gaps that may lead to measurement inaccuracies. In certain embodiments, the optical coupling material may be an optical coupling gel, oil, or liquid. Such materials may conform to the surface of the tissue while also leaving the optical path of the light substantially unaffected. In contrast to typical hard lenses or other encapsulating materials that are typically used to cover the optical components of a sensor, the optical coupling materials may provide a more gentle contact surface for the skin. Further, the optical coupling materials may act as heat dissipaters for any heat generated by the emitter and the detector, which may also provide additional comfort to the patient.

In certain embodiments, the optical coupling materials may include additional agents capable of improving the performance of the sensor. One advantage of the gel, liquid, or oil optical coupling materials may be to provide compatible bases for such agents in contrast to a solid sensor substrate, from which drug delivery may be more complex. For example, the optical coupling materials may include vasodilators or antimicrobial agents incorporated into the optical coupling material or the vasodilators or antimicrobial agents may surround the optical area. Vasodilators may increase perfusion at the site of the optically probed tissue, which may improve the measured signal. Antimicrobial agents may prevent growth of bacteria or other pathogens on patients with delicate tissue. In addition, the antimicrobial agents may prevent spoiling of the optical coupling materials during storage.

Keeping in mind the preceding points, the following sensor designs are provided as examples of sensors that include optical coupling materials for improved measurement signals. It should be appreciated that a sensor according to the present disclosure may be disposable or reusable sensors adapted for use on any appropriate patient tissue site, such as a digit, forehead, earlobe, foot, or for intrauterine use. For example, a sensor may be a clip-style sensor, appropriate for a patient earlobe or digit. Alternatively, a sensor may be a bandage-style or wrap-style sensor for use on a digit or forehead. Further, it should be appreciated that a sensor may be reflectance-type or transmission type.

For example, FIG. 1 illustrates an example of a transmission-type bandage sensor appropriate for use on a patient digit. As shown in FIG. 1, a sensor 10A may include a sensor body 14 that accommodates an emitter 16 and detector 18. One or both of the emitter 16 or the detector 18 may be associated with an optical coupling material 12. For example, the optical coupling material 12 may be disposed in an area (e.g., in a well or recess 24 as shown) between the tissue and the emitter 16 and/or detector 18, such that when the sensor 10A is applied to the digit, the optical coupling material 12 is in contact with the tissue. When light, represented by arrow 22, exits the emitter 16, the light passes through the optical coupling material 12 and the digit before encountering the detector. In embodiments, the detector 18 may be disposed in a second recess 24 filled with optical coupling material 12. The optical coupling material 12 acts as an interface between the emitter 16 and/or the detector 18, and the tissue to minimize any air gaps.

As noted, the sensor 10A may include one or more recesses 24 or other suitably shaped compartments into which the emitter and detector may be placed. Such an arrangement may exhibit improved light transmission properties by providing better control of the optical path of the detected light. For example, walls 28 of the emitter recess 24 may absorb off-angle light from an emitter 16, preventing it from shunting around the tissue. Similarly, walls 28 associated with the recess 24 around the detector 18 may prevent shunted light from reaching the detector 18. In embodiments, the walls 28 may be formed at least in part from a dark, light absorbing material. However, by recessing the emitter 16 and the detector 18 away from the tissue, air gaps between the optical sensing components and the tissue may be created that may interfere with the optical path of the light. Such a disadvantage may be overcome by filling the recesses 24 with the optical coupling material 12. When the recesses 24 are filled with the optical coupling material 12, the emitter 16 and detector 18 may be recessed into the sensor body 14 without creating air gaps that may bend the light and decrease the signal quality.

The depth of recesses 24 may be any appropriate depth with regard to other sensor structural considerations and path length considerations. However, because there are substantially minimal air gaps associated with such recesses 24 when filled with the optical coupling material 12, the depth of the recesses 24 may vary. For example, in certain embodiments, it may be advantageous to have relatively deep recesses (e.g., to protect specialized or expensive sensing components), while in other embodiments (e.g., for relatively thin bandage-type sensors) it may be advantageous to provide relatively shallow recesses.

Figure 2:
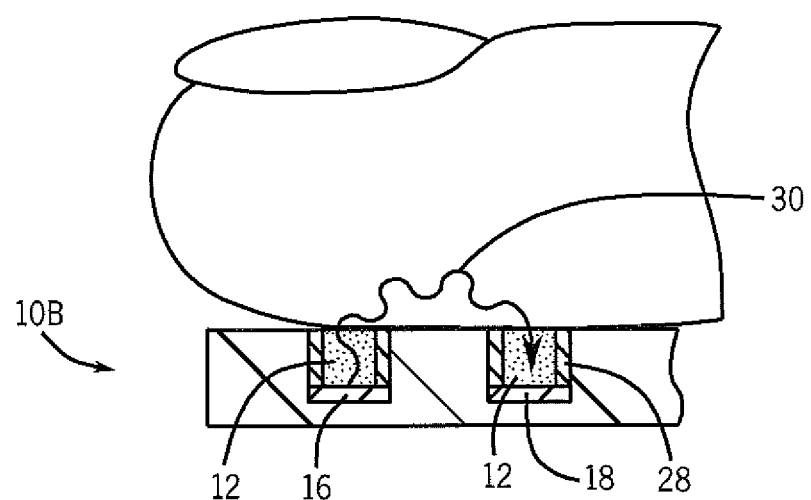
FIG. 2 is a side cross-sectional view of a reflectance-type sensor including an optical coupling material applied to a digit according to certain embodiments.

Similar advantages may be realized with a reflectance-type sensor 10B, shown in FIG. 2, in which the emitter 16 and the detector 18 are configured to lie side-by-side when applied to a patient's tissue. As shown, light from arrow 30 may be emitted from emitter 16 that is within recess 24 and may pass through optical coupling material 12 before being reflected/scattered by the tissue and encountering the detector 18. The detector 18 may also be disposed within a second recess 24, as shown, that is filled with optical coupling material 12.

The optical coupling material 12 may be any suitable non-solid and conformable optical coupler with suitable optical properties. Generally, the optical coupling material 12 may have a refractive index within a certain percentage of the refractive index of the emitter 16 at the wavelengths of interest to reduce any bending or change in optical path of the emitted light, for example the refractive index of the optical coupling material may be within about 20% or about 10% of the index of refraction of the emitter 16. In one embodiment, the refractive index of the emitter 16 is about 1.6 and the refractive index of the optical coupling material is between about 1.3 and about 1.9 or between about 1.4 and about 1.8.

For example, the optical coupling material 12 may include a gel, a liquid, an oil, a polymer, or a semi-solid material. In one embodiment, the optical coupling material 12 may be Luxlink® OG-1001, a non-curing optical coupling gel from Liteway, Inc (Hicksville, N.Y.) with a refractive index of 1.457 for radiation in the near UV, the visible, and the near infrared. Optical coupling liquids may include Series AAA, AA, A, and B liquids available from Cargille Laboratories (Cedar Grove, N.J.), with refractive indices ranging from 1.3-1.7. Optical coupling oils may include silicone oils.

In certain embodiments, the optical coupling material 12 may include any additives or other components that do not interfere with the optical properties of the material. For example, the optical coupling material 12 may also include medical adhesives such as Dermabond to attach the emitter or detector or both to the tissue or nail bed. This would prevent relative motion between the optics and the tissue and would reduce the air gap between the optics and the tissue. In addition, the optical coupling material 12 may include an antimicrobial agent that may protect the material from fouling during storage or that may impart some a protection against microbes to a patient. In particular, such an agent may protect a patient with delicate skin (e.g., a neonate or a patient with a skin injury) or an immuno-compromised patient. In certain embodiments, the antimicrobial agent may be a metal such as copper, silver, or gold in a metal bearing material. In embodiments, the metal may be elemental silver, powdered silver, silver ions ($Ag^+$), or a silver bearing material like silver oxide (AgO). In other embodiments, the antimicrobial agent may be an antibiotic, an antiviral, a fungicide, or other chemical agent.

The optical coupling material 12 may also include materials that are vasodilators. Such materials may enhance perfusion in the tissue at the site being optically probed by the sensor. While such materials may be incorporated into any sensor as provided, it may be advantageous to have a broad area of the skin in contact with the vasodilators to increase their effectiveness. In such embodiments, the optical coupling material 12 may cover the entire tissue-contacting surface of the sensor body. In other embodiments, the optical coupling layer may cover some portion of the tissue-contacting surface of the sensor body. The vasodilator may be applied to the tissue-contacting surface of the sensor body 14 in a layer thick enough to generally surround the emitter 16 and/or the detector 18. An appropriate vasodilator for topical use may include a vasodilator containing aminophylline 3%, isosorbide dinitrate 0.25%, and co-dergocrine mesylate 0.05%. Other vasodilating agents may include procaine, theo phylline, nicotinic acid, vincamine, isoptine and papaverine.

In one embodiment, a vasodilator (or other agent, e.g., an antimicrobial) may be incorporated into the optical coupling material through any suitable method. For example, in embodiments in which the optical coupling material is a liquid or oil, a powder formulation of the agent may be mixed with the liquid or oil to form a suspension. In embodiments in which the optical coupling material 12 is a gel, the agent may be mixed with the gel material, or, if the gel is highly viscous, the agent may be mixed with the liquid base of the gel before a thickener is added. In certain embodiments, the vasodilation may not be part of the optical coupling material, but instead may be achieved by using electrodes incorporated onto the tissue-contacting surface of the sensor 10. In such embodiments, the sensor performance may be enhanced by generally vasodilating the probed tissue with electrodes in conjunction with sensors 10 as provided.

Figure 3:
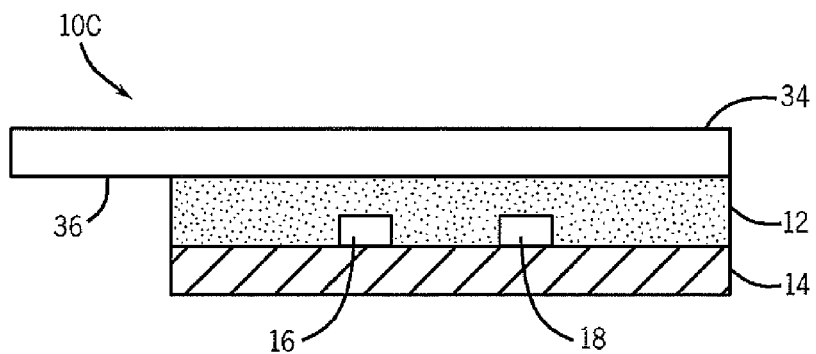
FIG. 3 is a cross-sectional view of a sensor including an optical coupling material applied over the sensor body and a removable membrane according to certain embodiments.

As noted, the optical coupling materials 12 may include oils or liquids, which are low viscosity materials. Such materials may not adhere well to a solid surface of a sensor 10 and, thus, are better-retained in association with the sensor body 14 if located within a recess 24 or other chamber. However, for higher viscosity, or lower flow, materials such as gels, such materials may retain good association with the sensor body 14 such that the optical coupling material 12 may be applied to all or part of a surface of the sensor body. As shown in FIG. 3, a sensor 10C may include a layer of the optical coupling material that is at least thick enough to cover any protruding parts of the emitter 16 or the detector 18. In one embodiment, if the optical coupling material is a water-based gel that may dry out if exposed to air, a retaining membrane 34 may be placed over the optical coupling material 12 to prevent the gel from drying out during shipping or storage. The retaining membrane 34 may include a tab 36 to facilitate manual removal of the membrane prior to application of the sensor. In other embodiments, the retaining membrane 34 may be used with other sensor arrangements, for example with sensor 10A or 10B, to prevent low flow optical coupling materials from leaking out of the recesses 34.

The optical coupling material 12 may be a polymer or copolymer that, when exposed to water, will form a water-swellable gel. For example, the water-swellable gel may include a copolymer that includes repeating prepolymer units, e.g. one or more monomers, such as 3-sulfopropyl acrylate potassium salt ("KSPA"), sodium acrylate ("NaA"), N-(tris(hydroxyl methyl)methyl) acrylamide ("tris acryl"), 2-acrylamido-2-methyl-1-propane sulfonic acid (AMPS), or any combination thereof. Other suitable monomers that may be incorporated into the water-swellable gel may include 3-sulfopropyl methacrylate sodium salt (KSPMA), N-vinyl pyrrolidone (NVP), allyl alcohol, allylamine, polyethylene glycol acrylate, polyethylene glycol methacrylate, vinyl functional phospholipids, and single or multiple vinyl functional conducting monomers (e.g. pyrrole), or any combination thereof. In such an embodiment, the polymers may be cross-linked or otherwise adhered to the sensor body. Prior to application, the sensor body 14 may be exposed to water so that the gel forms and swells to an appropriate degree. Such an embodiment may eliminate concerns about the gel drying out during storage.

Figure 4:
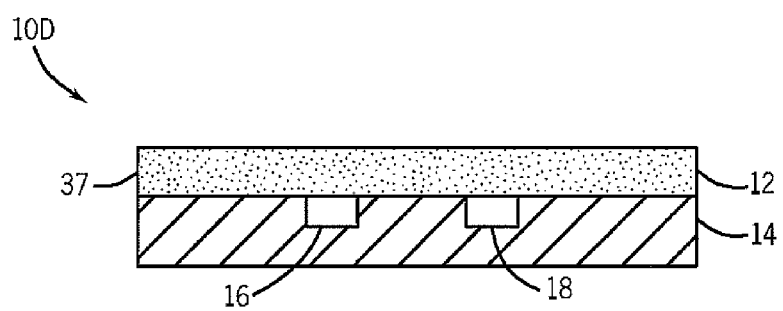
FIG. 4 is a cross-sectional view of a sensor including an removable pad including an optical coupling material applied over the sensor body according to certain embodiments.

As shown in FIG. 4, a sensor 10D may include a removable pad 37 including a layer of the optical coupling material 12. Such a pad 37 may be used in conjunction with reusable and disposable sensors, but may be particularly well-suited to use with reusable sensors. By using the removable pad, a reusable sensor may be "retrofit" to include the benefits of optical coupling materials 12. Further, the pad 37 may be any suitable configuration, such as a gel pad or may include a swellable layer activated by water.

Figure 5:
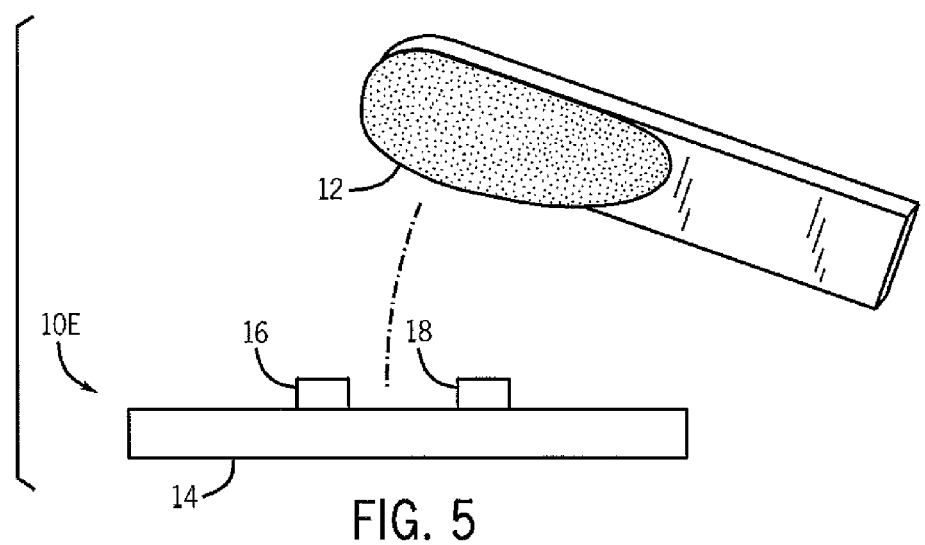
FIG. 5 is a side view of a sensor to which an optical coupling material may be applied at the time of use according to certain embodiments.

Alternatively, the optical coupling material 12 may be applied to the sensor prior to the sensor being affixed to the patient's tissue. FIG. 5 depicts an embodiment in which the optical coupling material 12 may be stored in a tub or other container and, for example, may be spread onto the surface of a sensor 10E prior to use, as shown. In such an embodiment, the sensor 10E may be stored or shipped without regard for special packaging to maintaining the optical coupling material 12 in a particular state, e.g., hydration of a gel.

Figure 6:
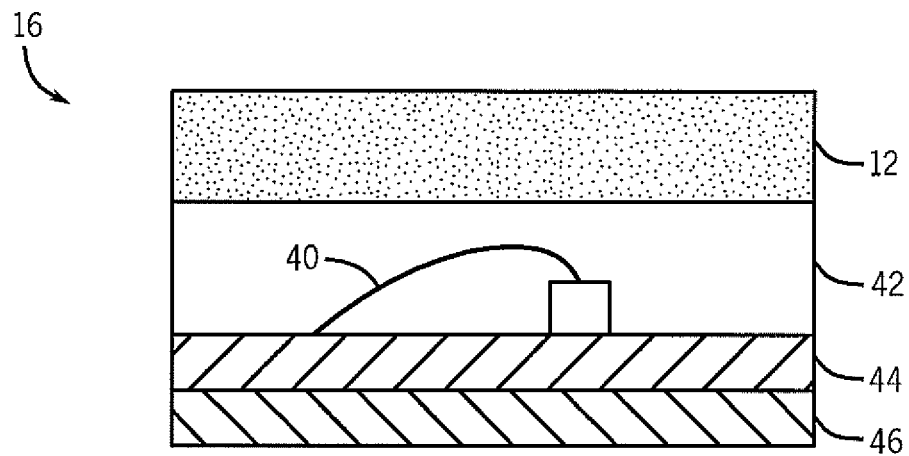
FIG. 6 is a cross sectional view of an emitter that includes a lens or encapsulating material and an optical coupling material according to certain embodiments.

An additional advantage provided by using an optical coupling material 12 in conjunction with the optical sensing components is that the optical coupling material may provide a more comfortable interface with the patient than hard encapsulating materials that are typically used to cover emitters 16 or detectors 18. FIG. 6 shows an emitter 16 in which the protruding parts of the emitter 16, such as the bond wire 40, are encapsulated in a layer of an encapsulating material 42, e.g., epoxy. The bond wire is connected to one or more lead frames 44, which in turn may be adhered to a substrate 46. When the emitter is in operation, the electrical components (e.g., the bond wire 40 and lead frame 44) may generate heat, which may be transferred to the encapsulating material 42. If an optical coupling material 12 is used to cover the encapsulating material, the heat may be lost or dissipated within the extra layer of the optical coupling material 12 without any loss in optical transmission. Further, the optical coupling material may protect the patient from direct contact with the hard surface of the encapsulating material 42.

Figure 7:
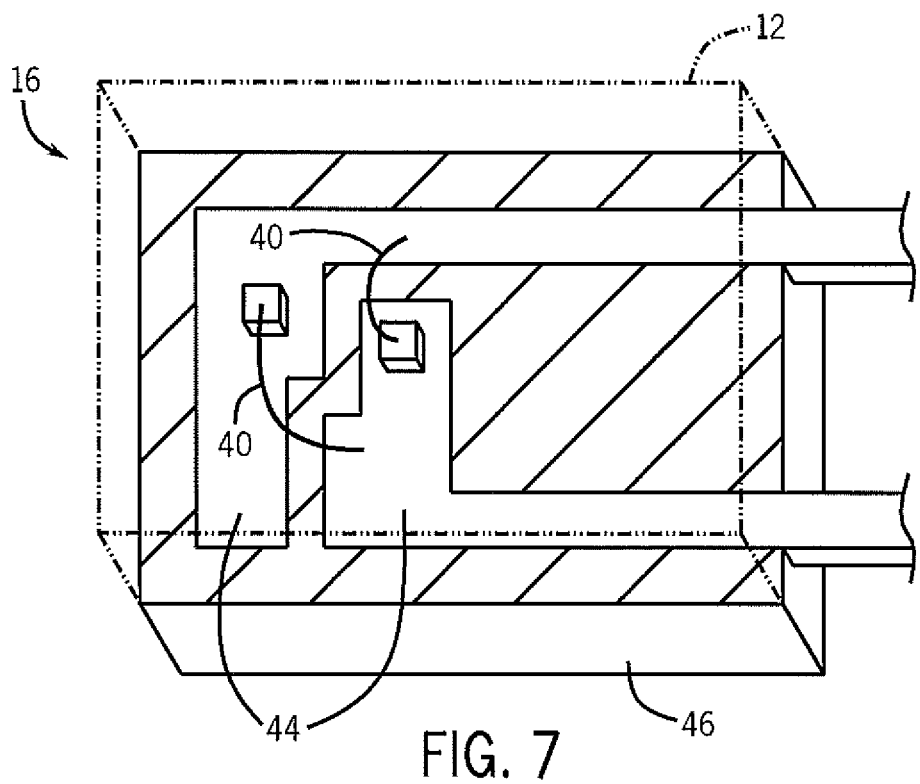
FIG. 7 is a cross sectional view of an emitter in which the optical coupling material is the encapsulating material according to certain embodiments.

In addition, the optical coupling material 12 may replace rigid optical encapsulators. FIG. 7 illustrates an emitter that includes an optical coupling material 12 instead of a hard encapsulating material. The use of a conformable optical coupling material 12 to encapsulate the bond wires 40 and lead frames 44 may protect the relatively fragile bond wires 40 from breaking during use. Because the thermal expansion rate of the bond wires 40 and an encapsulating material may be different, encapsulation in a rigid material may result in the bond wires 40 breaking if the rigid encapsulating material expands too quickly. In the case in which the bond wires are encapsulated in a conformable material, the difference in thermal expansion rates may have less of an effect on the bond wires 40 because the conformable material may allow for flexing and expansion of the bond wires 40. In certain embodiments, while the optical coupling material 12 may serve as the encapsulating material, a rigid cover may still be in place over the optical components to prevent outside forces from affecting the emitter 16.

Figure 8:
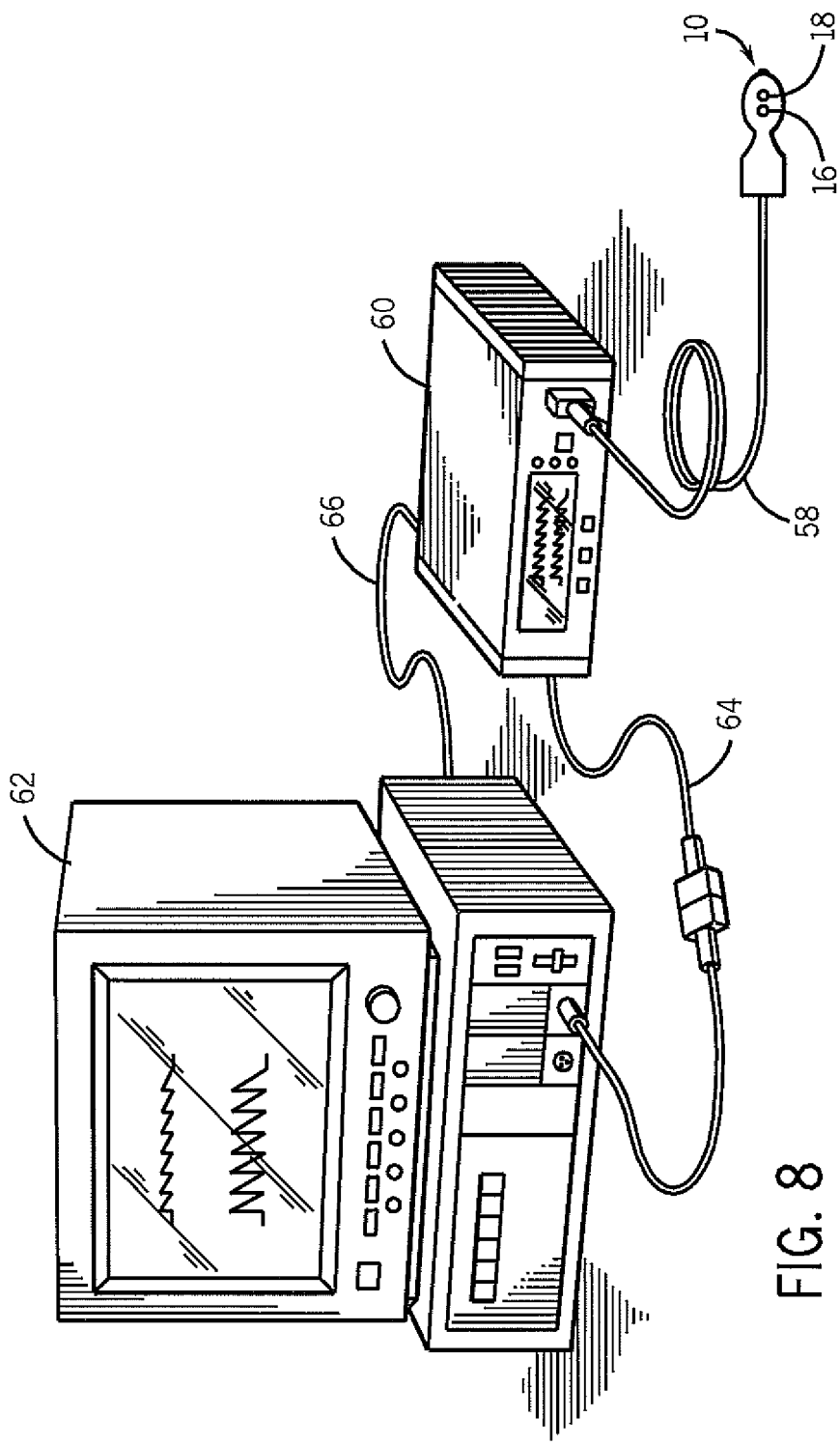
FIG. 8 illustrates a pulse oximetry system coupled to a multi-parameter patient monitor and a sensor according to certain embodiments.
Figure 9:
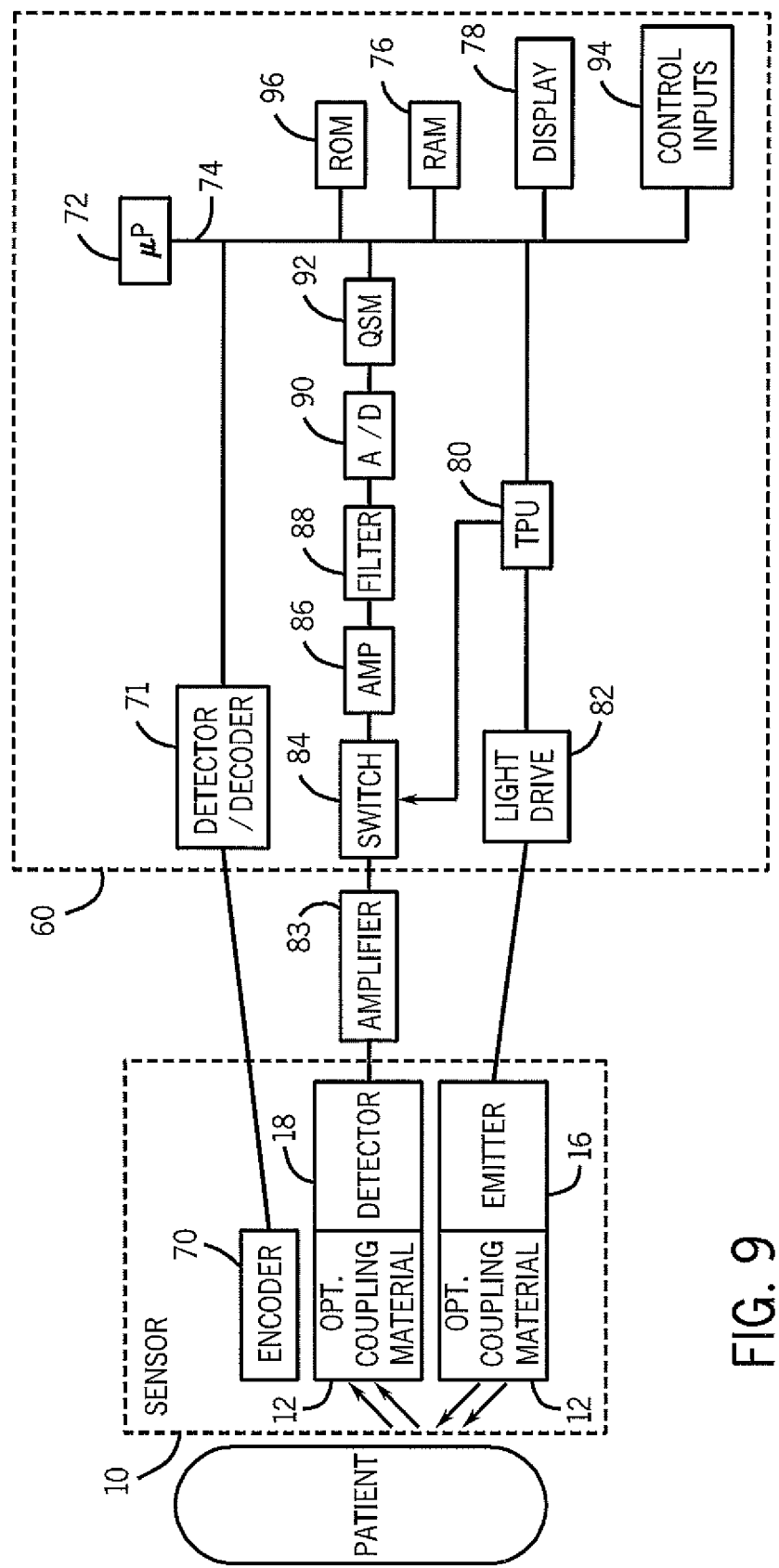
FIG. 9 is a block diagram of a pulse oximetry system according to certain embodiments.

A sensor or sensor assembly, illustrated generically as a sensor assembly 10, may be used in conjunction with a pulse oximetry system, as illustrated in FIG. 8. It should be appreciated that a cable 58 of the sensor assembly 10 may be coupled to a monitor 60 or it may be coupled to a transmission device to facilitate wireless transmission between the sensor assembly 10 and the monitor 60. The monitor 60 may be any suitable pulse oximeter, such as those available from Nellcor Puritan Bennett LLC. Furthermore, to upgrade conventional pulse oximetry provided by the monitor 60 to provide additional functions, the monitor 60 may be coupled to a multi-parameter patient monitor 62 via a cable 64 connected to a sensor input port or via a cable 66 connected to a digital communication port.

FIG. 8 is a block diagram of an embodiment of a monitor 60 that may be configured to implement the embodiments of the present disclosure. Light from emitter 16 may pass into a blood perfused tissue, and may be scattered, and then detected by detector 18. A sensor assembly 10 containing an emitter 16 and a detector 18 and an optical coupling material 12 may also contain an encoder 70 which may be capable of providing signals indicative of the wavelength(s) of light source 16 to allow the oximeter to select appropriate calibration coefficients for calculating oxygen saturation. The encoder 70 may, in an embodiment, be a resistor.

In an embodiment, the sensor assembly 10 may be connected to a pulse oximetry monitor 60. The monitor 60 may include a microprocessor 72 coupled to an internal bus 74. Also connected to the bus may be a RAM memory 76 and a display 78. A time processing unit (TPU) 80 may provide timing control signals to light drive circuitry 82, which controls when the emitter 16 is activated, and if multiple light sources are used the multiplexed timing for the different light sources. TPU 80 may also control the gating-in of signals from detector 18 through an amplifier 83 and a switching circuit 84. These signals are sampled at the proper time, depending at least in part upon which of multiple light sources is activated, if multiple light sources are used. The received signal from the detector 18 may be passed through an amplifier 86, a low pass filter 88, and an analog-to-digital converter 90. The digital data may then be stored in a queued serial module (QSM) 92, for later downloading to RAM 76 or ROM 96 as QSM 92 fills up.

In an embodiment, based at least in part upon the received signals corresponding to the light received by detector 18, microprocessor 72 may calculate the oxygen saturation using various algorithms. These algorithms may require coefficients, which may be empirically determined, and may correspond to the wavelengths of light used. The algorithms may be stored in a ROM 96 and accessed and operated according to microprocessor 72 instructions. For example, the encoder 70 may communicate with decoder 71 to allow the microprocessor 72 to determine the appropriate coefficients.

In an embodiment of a two-wavelength system, the particular set of coefficients chosen for any pair of wavelength spectra may be determined by a value indicated by the encoder 70 corresponding to a particular light source in a particular sensor assembly 10. In one embodiment, multiple resistor values may be assigned to select different sets of coefficients, or the sets of coefficients may be stored on a digital medium. In another embodiment, the resistors are used to select from among the coefficients appropriate for the optical characteristics of an infrared source paired with either a near red source or far red source. Further, the coefficients may relate to the physical location of the sources. The selection between whether the near red or far red set will be chosen can be selected with a control input from control inputs 94. Control inputs 94 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 16 and the detector 18 may be disposed on a sensor body, which may be made of any suitable material, such as plastic, foam, woven material, or paper. The sensor assembly 10 may be coupled to a cable that is responsible for transmitting electrical and/or optical signals to and from the emitter 16 and detector 18 of the sensor assembly 10. The cable may be permanently coupled to the sensor assembly 10, or it may be removably coupled to the sensor assembly 10—the latter alternative being more useful and cost efficient in situations where the sensor assembly 10 is disposable.

The sensor assembly 10 may be a "transmission type" sensor. Transmission type sensors include an emitter 16 and detector 18 that are typically placed on opposing sides of the sensor site. If the sensor site is a fingertip, for example, the sensor assembly 10 is positioned over the patient's fingertip such that the emitter 16 and detector 18 lie on either side of the patient's nail bed. In other words, the sensor assembly 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor assembly 10 will perform in substantially the same manner.

The sensor 10 may also be reflectance type sensor that operates by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or forehead such that the emitter 16 and detector 18 lie side-by-side. Reflectance type sensors detect light photons that are scattered back to the detector 18. A sensor assembly 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims

What is claimed is:

1. A sensor comprising:
a sensor body;
an emitter disposed on the sensor body;
a detector disposed on the sensor body; and
an optical coupling material disposed directly on at least one of the emitter or the detector, wherein the optical coupling material is configured to contact a patient's tissue when the sensor is applied to a patient, wherein the optical coupling material comprises one or more of a gel, oil, or liquid, and wherein an electrical lead and bond wires coupled to the emitter are in direct contact with the optical coupling material.

2. The sensor, as set forth in claim 1, wherein the sensor body comprises a well or recess in which the emitter or the detector is disposed.

3. The sensor, as set forth in claim 2, wherein the well or recess comprises one or more light absorbing walls.

4. The sensor, as set forth in claim 2, wherein the optical coupling material is disposed in the well or recess.

5. The sensor, as set forth in claim 1, wherein the optical coupling material has a refractive index between about 1.4 and about 1.8.

6. The sensor, as set forth in claim 1, wherein the optical coupling material has a refractive index of about 1.6.

7. The sensor, as set forth in claim 1, wherein a refractive index of the optical coupling material is within 10% of a refractive index of the emitter.

8. The sensor, as set forth in claim 1, comprising a removable membrane configured to retain the optical coupling material while the sensor is not in use.

9. A pulse oximetry system comprising:
a pulse oximetry monitor; and
a sensor assembly configured to be operatively coupled to the monitor, the sensor assembly comprising:
an emitter and a detector disposed on a sensor body;
an electrical lead and bond wires coupled to an emitter;
an optical coupling material disposed directly on at least one of the emitter, the detector, or the substrate, wherein the optical coupling material is configured to contact a patient's tissue when the sensor is applied to the patient, wherein the optical coupling material comprises one or more of a gel, oil, or liquid, and wherein the electrical lead and bond wires are in direct contact with the optical coupling material.

10. The system, as set forth in claim 9, wherein the sensor body comprises a well or recess in which the emitter or the detector is disposed.

11. The system, as set forth in claim 10, wherein the well or recess comprises one or more light absorbing walls.

12. The system, as set forth in claim 10, wherein the optical coupling material is disposed in the well or recess.

13. The system, as set forth in claim 9, wherein optical coupling material has a refractive index between about 1.4 and about 1.8.

14. The system, as set forth in claim 9, wherein the optical coupling material has a refractive index of about 1.6.

15. The system, as set forth in claim 9, wherein a refractive index of the optical coupling material is within 10% of a refractive index of the emitter.

16. The system, as set forth in claim 9, comprising a removable membrane configured to retain the optical coupling material while the sensor is not in use.

17. A method of manufacturing a sensor comprising:
providing a sensor body;
providing an emitter disposed on the sensor body;
providing a detector disposed on the sensor body; and
providing an optical coupling material disposed directly on at least one of the emitter or the detector, wherein the optical coupling material is configured to contact a patient's tissue when the sensor is applied to a patient, wherein the optical coupling material comprises one or more of a gel, oil, or liquid, and wherein an electrical lead and bond wires coupled to the emitter are in direct contact with the optical coupling material.

18. The method, as set forth in claim 17, wherein providing the sensor body comprises a well or recess on the sensor body in which the emitter or the detector is disposed.

19. The method, as set forth in claim 18, wherein the well or recess comprises one or more light absorbing walls.

20. The method, as set forth in claim 18, wherein optical coupling material has a refractive index between about 1.4 and about 1.8.

* * * * *